United States Patent [19]
Hall

[11] Patent Number: 5,533,963
[45] Date of Patent: Jul. 9, 1996

[54] DRESSING HOLDER

[76] Inventor: Robert L. Hall, 2001 Laurel Ave., Suite 204, Knoxville, Tenn. 37916

[21] Appl. No.: 367,935

[22] Filed: Jan. 3, 1995

[51] Int. Cl.⁶ .................................................. A61F 5/00
[52] U.S. Cl. .................. 602/75; 602/19; 602/53; 602/63; 2/321; 128/100.1; 128/846
[58] Field of Search .................. 602/19, 75, 76, 602/60, 42, 46, 83, 53; 128/96.1, 100.1, 101.1; 2/311, 312, 315, 317, 321, 326, 333; 606/213, 214, 215, 26

[56] References Cited

U.S. PATENT DOCUMENTS

| | | | |
|---|---|---|---|
| 915,049 | 3/1909 | Taylor | 128/96.1 X |
| 1,774,739 | 9/1930 | Voyne | 602/19 X |
| 2,531,757 | 11/1950 | Whinery | 602/19 |
| 2,800,902 | 7/1957 | Wiltrout | 602/19 X |
| 3,399,669 | 9/1968 | Kaplan | 602/19 X |
| 3,442,270 | 5/1969 | Steinman | 602/19 |
| 3,603,316 | 9/1971 | Lehman | 602/19 X |
| 3,799,156 | 3/1974 | Gurkin | 602/19 X |
| 3,920,008 | 11/1975 | Lehman | 128/96.1 |
| 4,022,197 | 5/1977 | Castiglia | 128/96.1 |
| 4,787,381 | 11/1988 | Hubbard et al. | 602/19 |
| 4,802,469 | 2/1989 | Gollestani | 128/96.1 |
| 4,825,866 | 5/1989 | Pierce | 606/216 |
| 5,143,092 | 9/1992 | Flower | 128/875 |
| 5,234,462 | 8/1993 | Pavletic | 606/216 X |
| 5,387,183 | 2/1995 | Jones | 602/19 |

FOREIGN PATENT DOCUMENTS 2268504  11/1975  France .................. 606/215

Primary Examiner—Richard J. Apley
Assistant Examiner—Kim M. Lee
Attorney, Agent, or Firm—Notaro & Michalos

[57] ABSTRACT

A dressing holder for a patient with an abdominal dressing, has a back panel made of at least partly elastic material such as LYCRA material. The panel extends around the back and along the flanks of the patients, leaving an exposed abdominal area. The area is spanned by elastic straps leaving at least some of the abdomen exposed for the passage of drains or for the exposure of ostomies and the like. Hook and loop tape is used at the edges of the back panel and at the ends of the straps to hold the straps to the back panel.

10 Claims, 2 Drawing Sheets

DRESSING HOLDER

FIELD AND BACKGROUND OF THE INVENTION

The present invention relates in general to medical dressings, and in particular, to a new and useful apparatus and technique for covering abdominal wounds. The apparatus does not require the aid of adhesives or tapes which often cause trauma, significant problems, and even pain to patients. It also accommodates abdominal devices such as drains or ostomies and is totally adjustable. The invention is also easily laundered and can be re-used. This is an important factor, since many surgical patients have wounds that require several weeks or months for healing.

The practice of surgery, particularly the field of abdominal surgery, requires incisions through the skin and abdominal wall. The resulting surgical wounds are covered with bandages or dressings to minimize infection and aid in the healing process. Many times intra-abdominal processes exist that are, by their nature, contaminated procedures. These contaminated procedures routinely require the skin and subcutaneous tissues to be left open and subsequent wound care provided. It is frequently necessary to leave drains within the abdominal cavity, exiting though the skin. When colonic or bowel surgery is involved, ostomies may be created. An ostomy is a portion of the opened intestinal tract that is connected to the skin and serves as an exit site for intestinal contents. These intestinal contents, i.e. feces, are collected in plastic bags placed over the ostomies on the abdominal wall. These abdominal procedures and operations are common and routine in modern medicine and are performed on a daily basis.

Currently, abdominal wounds are dressed with sterile gauze or bandages placed over or within the wounds. These dressings are secured in place, in one of two ways. The most commonly used method is with adhesive tapes. The second, less common method is the use of Montgomery straps. Montgomery straps are adhesive dressings that are applied adjacent both sides of the wound. These adhesive portions are connected to non-adhesive panels which have holes running parallel to the wound. Lacings are placed through these holes to secure the dressings to the abdominal wound.

Present understanding and historical information confirm that adhesive dressings are less than ideal. Trauma is incurred to the skin when removing the adhesive tape or adhesive dressing from the abdominal wall. This results in blisters, irritation, and new wounds. Many patients also react to adhesive tapes, in the form of contact dermatitis, incurring even further trauma. These disadvantages of adhesive dressings and adhesive tapes are well recognized in modern surgery as well as in historical reports.

Several attempts have been made to overcome the problems encountered with adhesive tape. However, none of these attempts have proved beneficial and are not used in today's surgical therapies.

One device disclosed in U.S. Pat. No. 2,531,757 to Whinery in 1947 attempted to provide a surgical dressing without adhesive tapes. This dressing was a bandage providing a circumferential binder to the wound using leg straps to prevent slippage of the bandage. The device was constructed of ordinary cloth with a small amount of elastic over the lateral aspects. It wrapped completely around the abdomen and was secured in place with interdigitating straps that were pinned laterally. This dressing covered the anterior portion of the abdomen, almost in its entirety. The Whinery device is not used in modern surgery, for multiple reasons. First the circumferential dressings lead to respiratory compromise in the postoperative abdominal surgery patient. Secondly, it required leggings that made it difficult for nursing tasks to be performed. Placement of the device, as well as caring for the bodily functions of the patient, i.e., defecation and urination, were very difficult. Furthermore, this dressing does not accommodate intra-abdominal drains or ostomies which exit from the anterior abdominal wall.

A similar attempt is disclosed in U.S. Pat. No. 3,486,501 to Erickson, et al., issued in 1969. This device was called an abdominal scultetus and in essence was designed similar to underwear or mens' briefs. It was somewhat adjustable and extended from the genitalia region up to the abdomen. This device had the same drawbacks as the Whinery device in that it was circumferential and rendered respiratory compromise, it provided no openings for ostomies, drains, or other such devices, and it covered the anal and genitalia region. The Erickson, et al. dressing made it even more difficult for those patients who were incontinent of urine or stool after their operative procedures. This drawback, coupled with the difficulty in applying the device greatly increased the need for nursing care. The device also failed to win any clinical acceptance and offered very little to the post-operative abdominal surgery patient.

In 1966, Bailey developed a surgical bandage which was fashioned somewhat after the Montgomery straps. See U.S. Pat. No. 3,417,749. This too, was a completely encircling bandage that again contributed to respiratory compromise. It did not have a portion that extended through the genitalia nor the gluteal region, however it was associated with the problem of slippage and did not stay firmly on the wound.

Surgical binders have been developed, which are circumferential and encase abdominal wounds. See U.S. Pat. No. 3,442,270 to Steinman. The Steinman binder was created to render support to the weakened body areas. However, this theory required that support be given for the abdominal musculature, and this theory is not routinely upheld. In most cases, support is not needed and the circumferential stress causes respiratory compromise and postoperative pulmonary problems. Therefore, the surgical binder, while giving support to the back and lower abdominal wall, serves no great purpose in securing abdominal dressings. Likewise, the circumferential binder has no accommodation for any abdominal drains, ostomies or devices attached to the abdominal wall.

In summary, all attempts have been unsatisfactory in providing a suitable device to hold abdominal dressings intact. What is needed is a device that will: secure abdominal dressings to the wound without the use of adhesives; provide adequate latitude for intra-abdominal drains and ostomies; be made of affordable and usable material; be simple to apply and use; and not contribute or cause respiratory compromise by complete circumferential compression.

SUMMARY OF THE INVENTION

The dressing holder of the present invention achieves all of these requirements. The dressing holder is superior to all previous dressings and bandages and, in particular, overcomes all of the problems associated with prior art structures and methods as described above. Specifically, the dressing holder of the invention provides:

A. A non-constrictive dressing for the abdomen, therefore preventing respiratory embarrassment or compromise;

B. A dressing that requires no adhesives or chemicals which cause dermatitis, ulcers, blisters, irritation, or trauma to the skin;

C. An abdominal dressing that is completely adjustable in the girth and vertical directions;

D. A dressing that does not slip and which firmly applies the sterile gauze to the wound without the use of buttock or gluteal attachment that can impair normal excretory functions of urination or defecation;

E. A dressing that is easily applied by the user or the health care provider;

F. An adjustable dressing that accommodates intestinal ostomies, bags, drains, or other devices exiting the abdominal wall;

G. A dressing made of economical, easily obtainable material; and

H. An abdominal dressing that can be laundered and is reusable.

Accordingly, a further object of the invention is to provide a dressing holder for a patient with an abdominal dressing, which comprises; a back panel made of partially elastic material and sized to extend across the back and anteriorly to each flank of a patient, leaving at least part of the anterior abdomen of the patient with the dressing exposed, the back panel having a pair of vertical edges, each with adjacent anterior surfaces for facing away from the patient while wearing the holder, the vertical edges having a vertical height; one of a hook and loop tape fastener, extending vertically along each of the anterior surfaces of each of the vertical edges; a plurality of elastic straps having different widths, a total of the widths of the straps being less than the vertical height of the vertical edges, each strap having opposite ends; and a tab of the other of the hook and loop tape fastener, fixed to each end of each strap for adjustably, selectively and removably attaching the tabs of each strap to both of the anterior surfaces of the back panel, the straps spanning the exposed abdomen and being spaced from each other so that at least part of the exposed abdomen remains exposed to accommodate intestinal ostomies, bags, drains and other devices exiting the anterior abdomen, adjacent the abdominal dressing.

A further object of the present invention is to utilize VELCRO (a trademark) tape as the hook and loop tape fastener.

A still further object of the invention is to provide the elastic straps so that they are also different lengths to accommodate different abdominal sizes, the partially elastic material being advantageously cotton or more advantageously LYCRA (a trademark) material.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
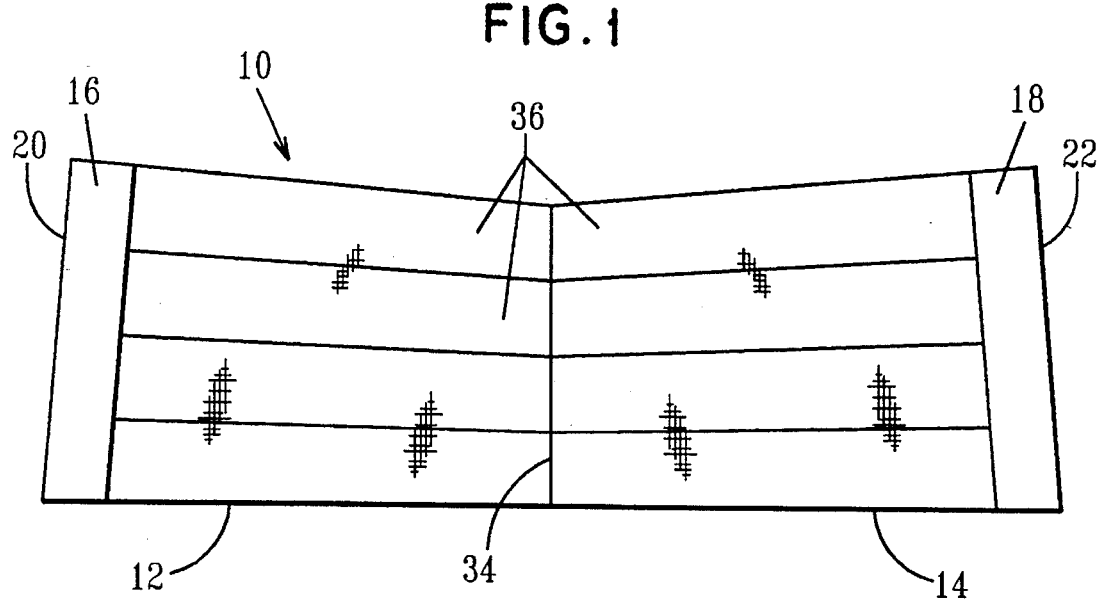
FIG. 1 is a front elevational view of a back panel of the dressing holder of the present invention, showing the outer surface thereof, the opposite surface being adapted for engagement against the abdomen of a patient.
Figure 2:
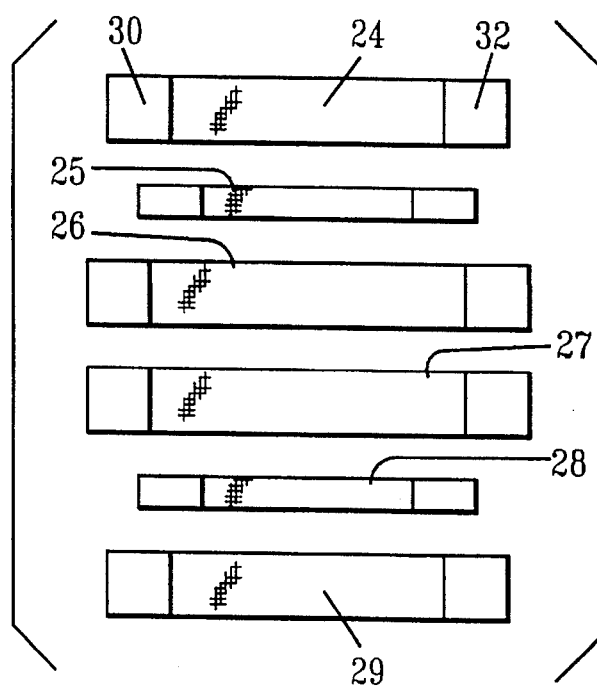
FIG. 2 is an exploded view showing a set of straps to be used in conjunction with the back to complete the dressing holder of the present invention.

Referring to the drawings in particular, FIGS. 1 and 2 illustrate a first embodiment of the invention.

A back panel 10 made of an elastic, or partially elastic material, extends from one flank 12 to the other 14 of the patient. On the anterior surface 16, 18 the back panel, along the vertical edges 20, 22 are strips of VELCRO tape, that may be the hook part of the tape. Anteriorly, the dressing holder includes various sized elastic straps 24 to 29 running horizontally. On each end of these elastic straps are VELCRO tape tabs, e.g., loop tab 30 and 32 on strap 24. The dressing is placed with the back panel extending from a posterior to anterior fashion, ending laterally to the flanks. The adjustable straps are then placed horizontally as deemed appropriate by the user across the anterior abdominal wall, holding the dressing intact. These are attached by approximating the VELCRO of the back panel to the VELCRO of the elastic straps. The straps are totally adjustable, vertically and in girth and are made in various widths and even different lengths if needed. This adjustability allows the straps to be placed above or below the drains, ostomies, or other abdominal devices.

All materials are made from washable products. The holder therefore can be used after washing on a long-term basis. It can be easily laundered at home.

The anterior abdominal wall is left relatively open by the invention, leaving these elastic straps to provide support to the abdominal dressing and still provide adjustability and accommodation for drains, ostomies, and other external devices. The advantages of this invention are multiple and include but are not limited to the following:

1. no circumferential constriction, therefore reducing respiratory compromise and pulmonary complications;
2. no adhesive or chemicals that cause irritation and subsequent damage to the skin;
3. adjustable in girth and vertical use;
4. holds the abdominal dressings firmly to the wound;
5. reusable and if it becomes soiled, can be easily laundered;
6. will accommodate for ostomies;
7. will accommodate for intra-abdominal drains or other devices that may exit through the anterior abdominal wall;
8. is made from a low cost material;
9. is easily applied by the health care giver or the patient; and
10. does not interfere with defecation, urination or other normal bodily functions.

In the embodiment of FIGS. 1 and 2, the back panel 10 is made of cotton, having some elastic or stretch characteristics. The back panel 10 has a slightly v-shaped configuration to accommodate the abdomen of an average patient and can be made in different sizes, for example, for male or female patients, or for adults or children. In the embodiment of FIG. 1, a central seam 34 is connected between pairs of slightly wedge shaped panels 36 which are sewn together to form the back panel 10.

The elastic straps 24–29 can be made of conventional elastic fabric material which is a known composite of synthetic or natural fibers woven with elastic, e.g. rubber fibers. This can be the type of material used, for example, to make ACE (a trademark) bandages, and the like. Any combination of the hook tape or loop tape can be connected to anterior areas 16, 18 and strap ends 30, 32, as long as a hook strip or tab is mated with a loop strip or tab.

Figure 3:
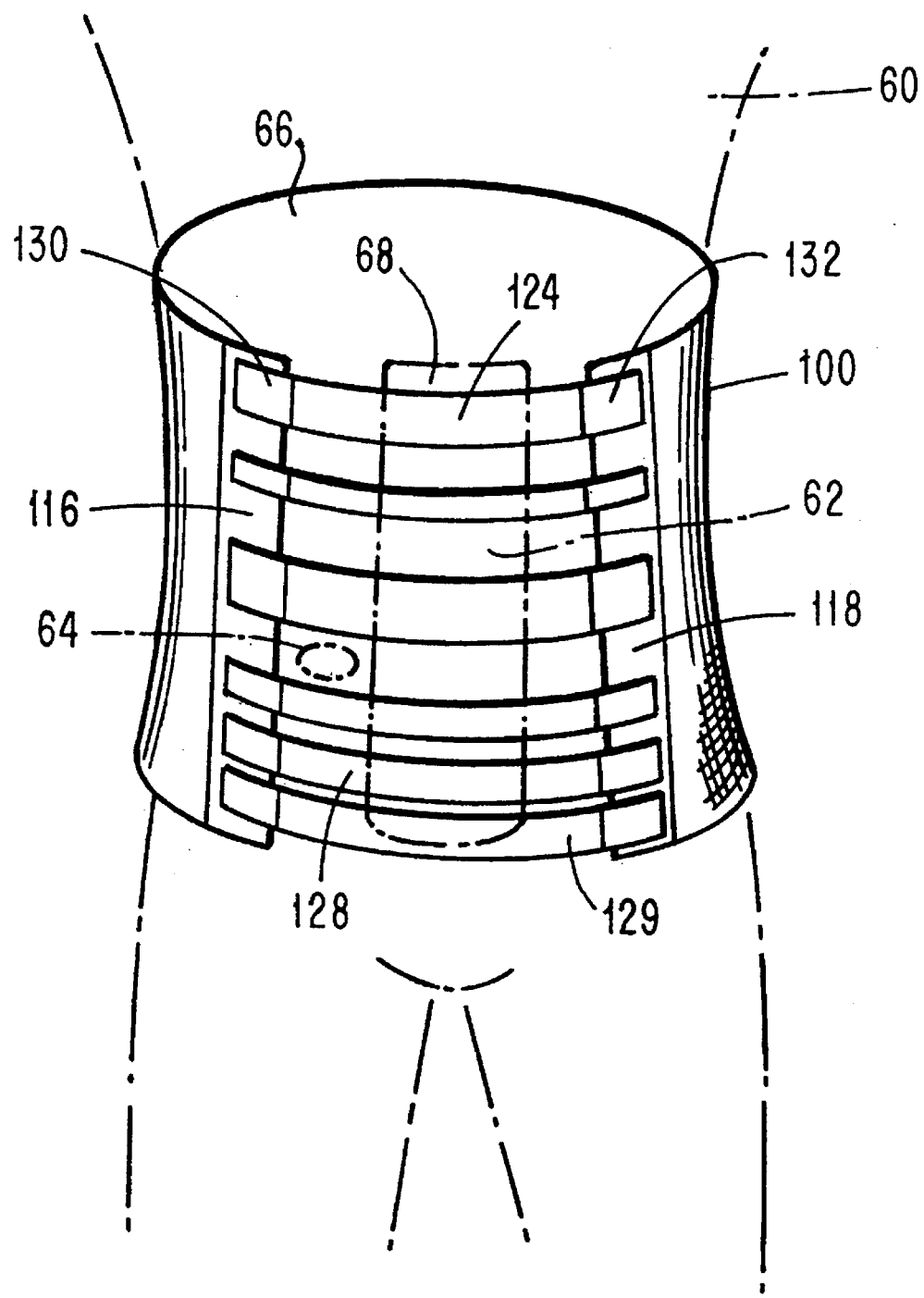
FIG. 3 is a perspective view another embodiment of the invention showing the dressing holder of the invention engaged over the abdomen of a patient.

FIG. 3 shows another embodiment of the invention, where the back panel is engaged around the abdomen of a patient 60. Panel 100 is made of other elastic or partly elastic material such as LYCRA, or other stretchy natural or synthetic material. It can be a single panel or multiple panels as desired.

The anterior surfaces 116, 118 are shown at the anterior of the patient's abdomen, exposing a large portion of the anterior which carries a binding, such as bandages, sutures, or bandages covering sutures, or any other postoperative dressing, shown at 68.

It is noted that no part of the back panel 100 covers this dressing nor an adjacent area which may carry structures that extend outwardly of the abdominal wall, such as an ostomy, drain or other device schematically shown at 64, for engaging a bag, drain conduits or the like (not shown). The elastic straps shown at 124, 128 and 129 do not completely close this exposed anterior abdominal area. The straps sufficiently hold and bind the bandage or other binding 68, while still leaving space for structures to pass the straps, such as shown at 64.

As also shown in FIG. 3, the back panel 100 extends from the back or posterior 66 of the patient, laterally around the flanks and anteriorly to the front of the abdomen.

The back panel and its vertical edges are selected to extend from Just below the waist of a patient to the vicinity at the lower end of the sternum. Taller or shorter panels can be utilized for larger or smaller anterior abdominal dressings. The length of the panel, when it is laid flat, as shown in FIG. 1, should be long enough to extend around the back, sides and over at least part of the anterior of the patient, but to leave a large open and exposed area, consistent with the structure and object of the present invention.

The total width of the elastic straps must also be less than the total height of the edges, so that even with the straps in place, some exposed areas remain between the straps as shown in FIG. 3.

While a specific embodiment of the invention has been shown and described in detail to illustrate the application of the principles of the invention, it will be understood that the invention may be embodied otherwise without departing from such principles.

What is claimed is:

1. A dressing binder adapted to hold an abdominal dressing in position over a wound of a patient, the patient having a back, abdomen and a flank located at each right and left side thereof, said dressing binder comprising: a back panel constructed from an imperforate partially elastic material and sized to extend across the back and each flank of a patient, leaving at least part of the abdomen of the patient with the dressing exposed, the back panel having a pair of spaced apart vertical edges with the exposed part of the abdomen being located between the vertical edges, the vertical edges having adjacent surfaces for facing away from the patient while wearing the binder and a vertical height; one of a hook and loop tape fastener extending vertically along each surface of each the vertical edges; a plurality of elastic straps having widths, a total of widths of the straps being less than the vertical height of the vertical edges, each strap having opposite ends and a tab of the other of the hook and loop tape fastener affixed thereto for adjustably, selectively and removably attaching each end of each strap to the vertical edges of the back panel, the straps spanning the exposed part of the abdomen and being spaced from each other so that at least part of the abdomen remains exposed to accommodate intestinal ostomies, bags, drains and devices exiting the abdomen adjacent the dressing.

2. A dressing holder according to claim 1, wherein at least some of the straps have different lengths.

3. A dressing holder according to claim 1, wherein the vertical height of the vertical edges of the back panel is selected to extend from below the waist to the vicinity of the sternum of a patient.

4. A dressing holder according to claim 3, wherein the partially elastic material of the back panel is cotton.

5. A dressing holder according to claim 1, wherein the back panel is V-shaped.

6. A dressing binder in combination with an abdominal dressing adapted for use by a patient, the patient having a back, abdomen and a flank located at each right and left side thereof, said dressing binder comprising: an abdominal dressing on an exposed part of the patient's abdomen; back panel constructed from an imperforate partially elastic material and sized to extend across the back and each flank of a patient, leaving at least part of the abdomen of the patient with the dressing exposed, the back panel having a pair of spaced apart vertical edges with the exposed part of the abdomen being located between the vertical edges, the vertical edges having adjacent surfaces for facing away from the patient while wearing the binder and a vertical height; one of a hook and loop tape fastener extending vertically along each surface of each the vertical edges; a plurality of elastic straps having widths, a total of widths of the straps being less than the vertical height of the vertical edges, each strap having opposite ends and a tab of the other of the hook and loop tape fastener affixed thereto for adjustably, selectively and removably attaching each end of each strap to the vertical edges of the back panel, the straps spanning the exposed part of the abdomen and being spaced from each other so that at least part of the abdomen remains exposed to accommodate intestinal ostomies, bags, drains and devices exiting the abdomen adjacent the dressing.

7. A dressing holder combination according to claim 6, wherein at least some of the straps have different lengths.

8. A dressing holder combination according to claim 7, wherein the vertical height of the vertical edges of the back panel is selected to expose from below the waist to the vicinity of the sternum of the patient.

9. A dressing holder combination according to claim 8, wherein the partially elastic material of the back panel is cotton.

10. A dressing holder according to claim 6, wherein the back panel is V-shaped.

* * * * *